(12) United States Patent
Nakasone et al.

(10) Patent No.: US 12,186,302 B2
(45) Date of Patent: Jan. 7, 2025

(54) DIPEPTIDYL PEPTIDASE-IV INHIBITOR AND FOOD WITH FUNCTION CLAIMS

(71) Applicants: Akari Nakasone, Miyoshi (JP); Satoshi Kondo, Miyoshi (JP); Yasuyo Shimamoto, Nagakute (JP); Madoka Abe, Nagoya (JP); Hirofumi Tachibana, Fukuoka (JP)

(72) Inventors: Akari Nakasone, Miyoshi (JP); Satoshi Kondo, Miyoshi (JP); Yasuyo Shimamoto, Nagakute (JP); Madoka Abe, Nagoya (JP); Hirofumi Tachibana, Fukuoka (JP)

(73) Assignees: TOYOTA JIDOSHA KABUSHIKI KAISHA, Toyota (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 17/545,053

(22) Filed: Dec. 8, 2021

(65) Prior Publication Data

US 2022/0184027 A1    Jun. 16, 2022

(30) Foreign Application Priority Data

Dec. 11, 2020   (JP) ................. 2020-205992

(51) Int. Cl.
*A61P 5/50*     (2006.01)
*A23L 33/105*   (2016.01)
*A61K 31/353*   (2006.01)

(52) U.S. Cl.
CPC .......... *A61K 31/353* (2013.01); *A23L 33/105* (2016.08)

(58) Field of Classification Search
CPC ....................................... A61P 5/50
See application file for complete search history.

(56) References Cited

U.S. PATENT DOCUMENTS

| | | | |
|---|---|---|---|
| 9,040,101 B2 | 5/2015 | Heiman et al. | |
| 9,061,003 B2 | 6/2015 | Sugihara et al. | |
| 10,251,408 B2 * | 4/2019 | Tachibana | ................. A61P 7/02 |
| 2008/0319052 A1 | 12/2008 | Yasue et al. | |
| 2017/0156361 A1 | 6/2017 | Tachibana | |

FOREIGN PATENT DOCUMENTS

| | | | | |
|---|---|---|---|---|
| EP | 2 119 712 | A1 | 11/2009 | |
| JP | 2005-328848 | A | 12/2005 | |
| JP | 2006-232805 | A | 9/2006 | |
| JP | 2006-298792 | A | 11/2006 | |
| JP | 2007-277163 | A | 10/2007 | |
| JP | 2008-173130 | A | 7/2008 | |
| JP | 2009-120491 | A | 6/2009 | |
| JP | 2011-079789 | A | 4/2011 | |
| JP | 2011-173902 | A | 9/2011 | |
| JP | 2011-225504 | A | 11/2011 | |
| JP | 2013-023450 | A | 2/2013 | |
| JP | 2013-184962 | A | 9/2013 | |
| JP | 2013-212111 | A | 10/2013 | |
| JP | 2017-043618 | A | 3/2017 | |
| JP | 2017-165673 | A | 9/2017 | |
| JP | 2018-118939 | A | 8/2018 | |
| JP | 2019-147772 | A | 9/2019 | |
| JP | 2020121990 | A * | 8/2020 | ............... A23F 3/16 |
| WO | WO 2008/066070 | A1 | 6/2008 | |
| WO | WO 2012/102308 | A1 | 8/2012 | |
| WO | WO 2015-199169 | A1 | 12/2015 | |

OTHER PUBLICATIONS

WIPO Machine English language translation of Kokai (JP 2018-118939 A) (Year: 2018).*
Tomoya Mita et al., Journal of the Japan Diabetes Society, vol. 56, No. 10 (2013), pp. 741-743.

* cited by examiner

*Primary Examiner* — John S Kenyon
(74) *Attorney, Agent, or Firm* — Finnegan, Henderson, Farabow, Garrett and Dunner, LLP

(57) ABSTRACT

A DPP-IV inhibitor and a food with functional claims, which comprises methylated catechin as a novel active ingredient, are provided.

2 Claims, 2 Drawing Sheets

[FIG. 1]
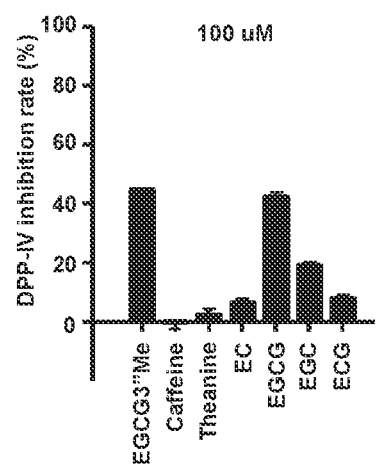

[FIG. 2]
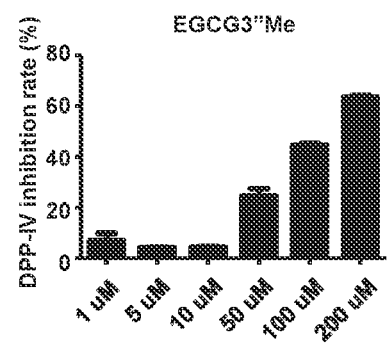

DIPEPTIDYL PEPTIDASE-IV INHIBITOR AND FOOD WITH FUNCTION CLAIMS

CROSS REFERENCE TO RELATED APPLICATIONS

The present application claims priority from Japanese patent application JP 2020-205992 filed on Dec. 11, 2020, the content of which is hereby incorporated by reference into this application.

BACKGROUND

Technical Field

The present disclosure relates to a dipeptidyl peptidase-IV inhibitor, a food with functional claims, and the like containing a novel active ingredient.

Background Art

As a type 2 diabetes treatment drug, there is one that suppresses the decomposition of incretins by inhibiting effects of dipeptidyl peptidase-IV (sometimes referred to as "DPP-IV"). Incretins are secreted from the gastrointestinal tract with the intake of food, act on pancreatic β cells to promote insulin secretion, and have the incretin effect of suppressing a blood sugar increase, and also has an effect of suppressing postprandial glucagon secretion, an effect of protecting and proliferating pancreatic β cells, and the like.

A substance that inhibits the effects of DPP-IV is referred to as a "dipeptidyl peptidase-IV inhibitor" (DPP-IV inhibitor). It has been clarified that DPP-IV inhibitor have various effects other than such a hypoglycemic effect (Journal of the Japan Diabetes Society, Vol. 56, No. 10 (2013), pp. 741-743). Specifically, it has been suggested that DPP-IV inhibitors have a neuronal cell-protecting effect on the brain, an effect of myocardial protection on the heart, an effect of improving vascular endothelial cell function on the arterial wall, a macrophage anti-inflammatory effect, an inhibitory effect on smooth muscle growth, and a hepatic fat-suppressing effect on the liver.

Regarding Natural products having an inhibitory effect on DPP-IV, JP Patent Publication (Kokai) No. 2018-118939 A discloses that tea catechins and tea catechin metabolites having a pyrogallol structure have high DPP-IV inhibitory activity. In other words, Patent Publication (Kokai) No. 2018-118939 A discloses that gallocatechin (GC), gallocatechin gallate (GCg), epigallocatechin (EGC), epigallocatechin gallate (EGCg), catechin gallate (Cg) and epicatechin gallate (ECg) have the DPP-IV inhibitory effect.

In addition, JP Patent Publication (Kokai) No. 2013-23450 A discloses DPP-IV inhibitory activity regarding ampelopsis (*Ampelopsis glandulosa* var. *helerophylia*) extract, sesame peptide, lemon balm extract, ginkgo leaf extract, yacon leaf extract, and *bodaiju* (*Tilia miqueliana*) extract. JP Patent Publication (Kokai) No. 2013-212111 A discloses that the water-soluble fraction of cheese is used as a DPP-IV inhibitor. JP Patent Publication (Kokai) No. 2007-277163 A discloses that the DPP-IV inhibitory effect regarding extracts of paprika, rose red petals, and cat's claw. JP Patent Publication (Kokai) No. 2017-43618 A discloses a DPP-IV inhibitor containing, as an active ingredient, a proteolytic product of tea leaves obtained by treating a protein from tea leaves with a protease. JP Patent Publication (Kokai) No. 2013-184962 A discloses the DPP-IV inhibitory effect regarding casein hydrolysates. WO2008/066070 discloses a peptide obtained by treating collagen or gelatin with collagenase or the like is used as a DPP-IV inhibitor. WO2012/102308 discloses the DPP-IV inhibitory effect regarding a peptide obtained by applying a two-step enzyme treatment to collagen.

Meanwhile, regarding methylated catechins among tea extracts, JP Patent Publication (Kokai) No. 2020-121990 A discloses a composition, which comprises a methylated catechin and a citrus extract or flavanone or a glycoside thereof, and which has an anti-cancer effect, an anti-muscle atrophy effect, an anti-obesity effect, an anti-inflammatory effect, a cholesterol-lowering effect, a thrombus or cerebral infarction-preventing effect, and an immune-enhancing effect. In addition, JP Patent Publication (Kokai) No. 2011-79789 A discloses methylated catechins have an inhibitory effect on the activity of ACE that is a factor related to the prevention of hypertension. JP Patent Publication (Kokai) No. 2017-165673 A discloses a hypoglycemic effect and a 1,5-anhydroglucitol-lowering effect of catechins including methylated catechins. JP Patent Publication (Kokai) No. 2009-120491 A discloses an adiponectin production promoter containing a methylated catechin as an active ingredient. JP Patent Publication (Kokai) No. 2011-173902 A discloses an anti-allergic effect with ability to inhibit TNF-α production regarding extracts of the tea cultivar "*Benifuuki*" and the like having high methylated catechin contents. JP Patent Publication (Kokai) No. 2006-298792 A discloses an anti-obesity agent containing a methylated catechin as an active ingredient. EP2119712A1 discloses an anti-allergic effect regarding methylated catechins.

SUMMARY

As described above, various physiological functions of methylated catechins are known and various applications thereof have been suggested, but there is no report on what kind of effects methylated catechins have on DPP-IV, and the effects remain unknown. For example, U.S. Pat. No. 9,040,101B2 discloses that blood sugar levels are controlled by regulating intestinal bacteria with a substance containing an indigestible carbohydrate such as inulin, oligofructose, fructooligosaccharide, or resistant starch, and also discloses catechins as substances that can be added. However, this does not suggest that catechins have the DPP-IV inhibitory effect, and does not suggest what effects methylated catechins have on DPP-IV.

The present disclosure provides a DPP-IV inhibitor and a food with functional claims, which comprises a methylated catechin as an active ingredient, by clarifying the DPP-IV inhibitory effect of the methylated catechin. The present disclosure provides a method for inhibiting a DPP-IV or an activity of a DPP-IV with an use of the DPP-IV inhibitor or the food with functional claims.

As a result of intensive studies, the present inventors found that methylated catechins have excellent DPP-IV inhibitory activity among green tea extracts. This has led to the completion of the present disclosure.

The present disclosure encompasses the following.
(1) A dipeptidyl peptidase-IV inhibitor comprising a methylated catechin as an active ingredient.
(2) The dipeptidyl peptidase IV inhibitor according to (1), wherein the methylated catechin comprises epigallocatechin-3-O-(3-O-methyl)gallate.
(3) A food with functional claims comprising a methylated catechin as an active ingredient and having a dipeptidyl peptidase IV inhibitory effect.

(4) The food with functional claims according to (3), wherein the methylated catechin comprises epigallocatechin-3-O-(3-O-methyl)gallate.

(5) A method for inhibiting a dipeptidyl peptidase-IV or an activity of a dipeptidyl peptidase-IV, comprising a step of allowing a subject to intake the dipeptidyl peptidase IV inhibitor according to (1) or the food with functional claims according to (3).

Further, the present disclosure provides a drug selected from the group consisting of a diabetes treatment drug, a drug for protecting neuronal cells, an arteriosclerosis treatment drug, and a fatty liver treatment drug which comprise a methylated catechin as an active ingredient.

Furthermore, the present disclosure provides a method for enhancing at least one effect selected from the group consisting of an effect of promoting insulin secretion, an effect of suppressing glucagon secretion, an effect of protecting neuronal cells, an effect of myocardial protection, an effect of improving vascular endothelial cell function, a macrophage anti-inflammatory effect, an effect of suppressing smooth muscle cell proliferation, a hepatic fat-suppressing effect, a renal protective effect, an effect of promoting sodium excretion, an effect of delaying the discharge of gastric and/or small intestinal contents, an effect of improving insulin sensitivity, a neuroprotective effect, an effect of promoting osteoblast proliferation, and an effect of suppressing osteoblast apoptosis, the method comprising allowing a subject to ingest a composition containing a methylated catechin as an active ingredient (in one embodiment, excluding medical practice for humans).

The dipeptidyl peptidase-IV inhibitor and food with functional claims according to the present disclosure contain a methylated catechin as an active ingredient that inhibits the activity of dipeptidylpeptidase IV. According to the present disclosure, a dipeptidyl peptidase-IV inhibitor and a food with functional claims containing a novel active ingredient can be provided.

BRIEF DESCRIPTION OF THE DRAWINGS

FIG. 1 is a characteristic diagram showing the results of measuring the DPP-IV inhibitory effect regarding various catechins including a methylated catechin; and FIG. 2 is a characteristic diagram showing the relationship between the concentration of EGCG3"Me and the DPP-IV inhibitory activity.

DETAILED DESCRIPTION

Hereinafter, the present disclosure will be described in detail.

The DPP-IV inhibitor and food with functional claims according to the present disclosure comprise a methylated catechin as an active ingredient. Examples of methylated catechins include epigallocatechin-3-O-(3-O-methyl)gallate (hereinafter referred to as EGCG3"Me), epicatechin-3-O-(3-O-methyl)gallate (hereinafter referred to as ECG3"Me), epicatechin-3-O-(4-O-methyl)gallate (hereinafter referred to as ECG4"Me), epigallocatechin-3-O-(4-O-methyl)gallate (hereinafter referred to as EGCG4"Me), gallocatechin-3-O-(3-O-methyl)gallate (hereinafter referred to as GCG3"Me), catechin-3-O-(3-O-methyl)gallate (hereinafter referred to as CG3"Me), catechin-3-O-(4-O-methyl)gallate (hereinafter referred to as CG4"Me), and gallocatechin-3-O-(4-O-methyl)gallate (hereinafter referred to as GCG4"Me) as well as isomers thereof. In particular, epigallocatechin-3-O-(3-O-methyl)gallate (EGCG3"Me) is comprised as an active ingredient in some embodiments.

Here, the DPP-IV inhibitory effect will be described. An incretin (glucagon-like peptide-1 (GLP-1)), which is secreted from the gastrointestinal tract in response to the detection of the inflow of food, is decomposed in vivo by the degrading enzyme DPP-IV in a short half life of 2 to 3 minutes. Incretins act to enhance insulin secretion from pancreatic β cells so as to lower the blood sugar level, Therefore, DPP-IV inhibitors can maintain insulin secretion from pancreatic β cells by suppressing the decomposition of incretins by DPP-IV so as to lower the blood sugar level.

Incretins not only act on pancreatic β cells to promote insulin secretion, but also have an effect of suppressing glucagon secretion from pancreatic α cells, an effect of suppressing appetite via the central nerve, an effect of delaying gastric excretion, an effect of protecting various organs, and the like. Therefore, DPP-IV inhibitors can be expected to have an effect of lowering cholesterol and triglyceride in type 2 diabetic patients, in addition to the effect of lowering the blood sugar level, by suppressing the decomposition of incretins by DPP-IV. DPP-IV inhibitors have been shown to reduce the secretion of triglycerides, cholesterol, and apoB48 from the small intestine through the enhancement effects of incretins. In addition, it has been suggested that DPP-IV inhibitors may be involved in cholesterol metabolism, such as suppressing the absorption of cholesterol in the gastrointestinal tract. Regarding blood pressure, it has been reported that DPP-IV inhibitors improve outpatient blood pressure levels and systolic and diastolic blood pressure levels evaluated by a 24-hour sphygmomanometer. This mechanism may be mediated by the effects of suppression of sodium (Na) reabsorption in proximal tubules and improvement of vascular endothelial relaxation reaction of renal arteries in response to the enhancement effects of incretins.

It has been reported that DPP-IV inhibitors further function to protect various organs such as brain, heart, liver, kidneys, nerves, fat, and blood vessels through the enhancement of the effects by incretins. For example, a protective effect on vascular endothelial cells, a macrophage anti-inflammatory effect, and an inhibitory effect on smooth muscle cell proliferation in blood vessels have been suggested.

In addition, it has been reported that DPP-IV inhibitors have the potential to suppress macrophage foaming and osteoblast apoptosis through the enhanced glucose-dependent insulinotropic polypeptide (GIP) effect among incretins effects. It has also been reported that DPP-IV inhibitors have a cardioprotective effect and an effect of promoting angiogenesis by inducing endothelial progenitor cells into myocardia of the infarct lesion and blood vessels of the ischemic lesion.

Meanwhile, DPP-IV is a 110-kDa membrane-related glycoprotein consisting of 766 amino acids, and is also expressed: in organs such as the intestinal tract, liver, lungs, and kidneys in vascular endothelial cells T cells; in macrophages, and the like. In addition, it has been reported that there is DPP-IV in a soluble form that circulates in the blood. It has been reported that DPP-IV particularly is secreted from adipocytes according to the degree of obesity, and DPP-IV itself may inhibit insulin signals in adipose tissue, skeletal muscle, and vascular smooth muscle cells, and may be one of the causes of metabolic syndrome.

It has also been reported that DPP-IV inhibitors suppress the development of arteriosclerosis in LDL receptor-deficient mice. Further, it has been shown that DPP-IV inhibitors have a positive effect on glycolipid metabolism and suppress the inflammatory response and migration of bone marrow-derived monocytes. Soluble DPP-IV present in the blood itself is presumed to have some effect on arteriosclerosis.

Summarizing the findings so far, the DPP-IV inhibitor containing a methylated catechin as an active ingredient according to the present disclosure can be said to have at least one effect selected from the group consisting of an effect of promoting insulin secretion, an effect of suppressing glucagon secretion, an effect of protecting neuronal cells, an effect of myocardial protection, an effect of improving vascular endothelial cell function, a macrophage anti-inflammatory effect, an effect of suppressing smooth muscle cell proliferation, a hepatic fat-suppressing effect, a renal protective effect, an effect of promoting sodium excretion, an effect of delaying the discharge of gastric and/or small intestinal contents, an effect of improving insulin sensitivity, a neuroprotective effect, an effect of promoting osteoblast proliferation, and an effect of suppressing osteoblast apoptosis. Therefore, the DPP-IV inhibitor according to the present disclosure is useful as a food, medicine, or supplement intended for at least one effect selected from the group consisting of an effect of promoting insulin secretion, an effect of suppressing glucagon secretion, an effect of protecting neuronal cells, an effect of myocardial protection, an effect of improving vascular endothelial cell function, a macrophage anti-inflammatory effect, an effect of suppressing smooth muscle cell proliferation, a hepatic fat-suppressing effect, a renal protective effect, an effect of promoting sodium excretion, an effect of delaying the discharge of gastric and/or small intestinal contents, an effect of improving insulin sensitivity, a neuroprotective effect, an effect of promoting osteoblast proliferation, and an effect of suppressing osteoblast apoptosis.

Meanwhile, methylated catechins can be isolated from green tea extracts. Green tea extracts are prepared from tea trees, which are evergreen trees of the family Theaceae, and contain at least methylated catechins. Examples of green tea trees include tea trees of *Camellia taliensis* and *Camellia sinensis*. For example, tea cultivars such as tea plant (*Camellia sinensis* (L.) Kuntze), Assam tea (*Camellia sinensis* (L.) Kuntze var. *assamica* (J. W. Mast.) Kitam.), a hybrid cultivar of *Camellia sinensis* and *Camellia taliensis*, "Yabukita," "Benifuuki," "Benyfuji," "Benihomare," "Yaeho," "Surugawase," "Yutakamidori," "Kanayamidori," "Okumusashi," "Chin-Shin-Dapan," "Chin-Shin-Oolong," "Dah Yeh Oolong," "safflower," "Benihikari," "Yamakai," "Yamamidori," "Karabeni," "Koushun," "Soufuu," "Fukumidori," "Minekaori," "Benihikari," "Minamikaori," "Izumi," "Fuushun," "Tamamidori," "Yamagai," "Kuritawase," "Shunmei," "Sayamamidori," "Asagiri," "Hokumei," "Tadanishiki," "Asahi," "Sayamakaori," "Meiryoku," "Yamatomidori," "Asatsuyu," "Toyoka," "Natsumidori," "Ujihikari," "Ooiwase," "Gokou," "Inzatsu 131," "Makinoharawase," "Takachiho," "Komakage," "Samidori," "Komakage," "Hatsumomiji," "Ryoufuu," "Minamisayaka," "Saemidori," "Okuyutaka," "Fujimidori," "Sunrouge," and "Okumidori" are used, and "Yabukita," "Benifuuki," "Kanayamidori," "Okumusashi," "Soufuu," "Fuushun," "Tadanishiki," and "Sunrouge" can be mentioned in some embodiments. In addition, examples of tea leaves from trees of these tea cultivars include *Sencha, Gyokuro, Bancha, Kukicha, Media, Genmaicha, Konacha, Matcha, Kamairi-cha, Tencha, Paochong* tea, oolong tea, and black tea.

An extraction solvent is not particularly limited, but water, an organic solvent, or a mixture thereof is used.

Examples of organic solvents include: lower alcohols having 1 to 4 carbon atoms such as methanol, ethanol, propanol, isopropanol, n-butanol, isobutanol, sec-butanol, and tert-butanol; polar organic solvents including ketones such as dimethyl ketone, methyl ethyl ketone, acetone, and methyl isobutyl ketone; and non-polar organic solvents such as methyl acetate, ethyl acetate, butyl acetate, and diethyl ether. Further, mixtures in which these polar organic solvents and non-polar organic solvents are appropriately combined can also be used. In some embodiments, hot water, ethanol, and hydrous ethanol can be used. The alcohol concentration of hydrous alcohol is from 30% (v/v) to 90% (v/v) and from 40% (v/v) to 70% (v/v) in some embodiments. In the case of hot water, the temperature is from 40° C. to 100° C. and from 60° C. to 100° C. in some embodiments.

Examples of the extraction method for obtaining green tea extract include known methods such as extraction by immersion, heat extraction, continuous extraction, and supercritical extraction. The green tea extract may then be concentrated by a known method. The obtained green tea extract or concentrate may be further purified by a known method. Examples of the purification method include ultrafiltration, adsorption resin treatment, molecular chromatography, partition chromatography, and liquid-liquid extraction.

Examples of the drying method include, but are not limited to, spray drying and freeze drying. The green tea extract may contain components other than methylated catechins, such as epigallocatechin gallate and other polyphenols, and catechins other than methylated catechins. The green tea extract contains a catechin such as epicatechin, epigallocatechin, catechin gallate, epicatechin gallate, gallocatechin gallate, or a methylated catechin in some embodiments.

The DPP-IV inhibitor according to the present disclosure can be a composition or a composition for food having various effects described above. In addition to a methylated catechin, the composition may contain a carrier acceptable for food and other known or well-known additives. Examples of the additives can include an excipient, a binder, a lubricant, a disintegrant, a colorant, a flavoring/odor improving agent, an emulsifier, a surfactant, a dissolution aid, a suspending agent, an isotonic agent, a buffer, a preservative, an antioxidant, a stabilizer, and an absorption enhancer, which are generally used in medicine or food, if desired, these can be used in combination as appropriate.

The composition may be in any form of liquid, solid, powder, or gel, and the dosage form of the composition is an oral dosage form such as tablets, a powder, capsules (hard capsules or soft capsules), granules, pills, a liquid, a syrup, or the like. These formulations can be prepared according to an ordinary method. In a case in which the composition is in a solution form, an aqueous medium such as water can be mentioned as a carrier to be used in some embodiments.

In a case in which the composition is in a solid form, an excipient such as crystalline cellulose, magnesium stearate, or calcium stearate, and a leavening agent such as cornstarch or alginic acid can be used as additional components.

In addition, examples of a compound required for forming the composition into a powder, a solid agent, or a liquid agent include erythritol, maltitol, hydroxypropyl cellulose, kaolin, and talc.

The composition has at least one effect selected from the group consisting of an effect of promoting insulin secretion, an effect of suppressing glucagon secretion, an effect of protecting neuronal cells, an effect of myocardial protection, an effect of improving vascular endothelial cell function, a macrophage anti-inflammatory effect, an effect of suppressing smooth muscle cell proliferation, a hepatic fat-suppressing effect, a renal protective effect, an effect of promoting sodium excretion, an effect of delaying the discharge of gastric and/or small intestinal contents, an effect of improving insulin sensitivity, a neuroprotective effect, an effect of promoting osteoblast proliferation, and an effect of suppressing osteoblast apoptosis as described above. Therefore, the composition can be used as an agent for promoting insulin secretion, an agent for suppressing glucagon secretion, an agent for protecting neuronal cells, an agent for myocardial protection, an agent for improving vascular endothelial cell function, a macrophage anti-inflammatory agent, an agent for suppressing smooth muscle cell proliferation, a hepatic fat-suppressing, a renal protective agent, an agent for promoting sodium excretion, an agent for delaying the discharge of gastric and/or small intestinal contents, an agent for improving insulin sensitivity, a neuroprotective agent, an agent for promoting osteoblast proliferation, or an agent for suppressing osteoblast apoptosis.

Examples of a subject which is allowed to ingest the composition include, but are not particularly limited to, mammals other than humans such as experimental animals (e.g., mice, rats, guinea pigs, and rabbits), livestock (e.g., cattle, horses, pigs, and goats), and pet animals (e.g., pets such as dogs and cats), in addition to humans. According to the composition of the present disclosure, the prevention or treatment of diabetes and the like, or the improvement of lifestyle-related diseases and obesity can be expected.

The intake of the composition in terms of the amount of a methylated catechin per 1 kg of body weight per day is from 0.1 to 30 mg in some embodiments, from 0.1 to 20 mg in other embodiments, from 0.1 to 10 mg in still other embodiments, and from 0.1 to 5 mg in yet other embodiments.

The food according to the present disclosure contains a methylated catechin. As the food has these ingredients in a predetermined ratio, the food can be used as a food with functional claims, supplement, or the like intended for at least one effect selected from the group consisting of an effect of promoting insulin secretion, an effect of suppressing glucagon secretion, an effect of protecting neuronal cells, an effect of myocardial protection, an effect of improving vascular endothelial cell function, a macrophage anti-inflammatory effect, an effect of suppressing smooth muscle cell proliferation, a hepatic fat-suppressing effect, a renal protective effect, an effect of promoting sodium excretion, an effect of delaying the discharge of gastric and/or small intestinal contents, an effect of improving insulin sensitivity, a neuroprotective effect, an effect of promoting osteoblast proliferation, and an effect of suppressing osteoblast apoptosis.

Examples of the form of the food (especially a food with functional claims) of the present disclosure include supplements (powders, granules, soft capsules, hard capsules, tablets, chewable tablets, quick-disintegrating tablets). Other examples thereof include beverages (e.g., tea, carbonated drinks, lactic acid drinks, and sports drinks), confectionery (e.g., gum, chocolate, cookies, and candies), oils, fat and oil foods (e.g., mayonnaise, dressing, and butter), seasonings (e.g., ketchup and sauce), liquid diet, dairy products (e.g., milk, yogurt, and cheese), breads, and noodles (e.g., udon, soba, ramen, pasta, hiyamugi (thin wheat noodles), and rice vermicelli), but are not limited to these forms.

Examples of a subject which is allowed to ingest the food of the present disclosure include, but are not particularly limited to, mammals other than humans such as experimental animals (e.g., mice, rats, guinea pigs, and rabbits), livestock (e.g., cattle, horses, pigs, and goats), and pet animals (e.g., pets such as dogs and cats), in addition to humans.

The intake of the food of the present disclosure in terms of the amount of a methylated catechin per 1 kg of body weight per day is from 0.1 to 30 mg in some embodiments, from 0.1 to 20 mg in other embodiments, from 0.1 to 10 mg in still other embodiments, and from 0.1 to 5 mg in yet other embodiments.

EXAMPLES

Hereinafter, the present disclosure will be described in more detail by way of examples, but the technical scope of the present disclosure is not limited to the following examples.

Example 1

In this Example, various catechins including a methylated catechin were used to examine their DPP-IV inhibitory activity. Regarding the DPP-IV inhibitory activity, a commercially available DPP (IV) Inhibitor Screening Assay Kit (manufactured by Cayman Chemical) was used. Catechins tested in this Example were epicatechin-3-O-gallate (ECG), epicatechin (EC), epigallocatechin(EGC), (–)-epigallocatechin gallate (EGCG), and (–)-epigallocatechin 3-(3"-O-methyl)gallate (EGCG3"Me). These catechins were purchased from Nagara Science Co., Ltd. In addition, caffeine was purchased from Sigma-Aldrich, and L-theanine was purchased from FUJIFILM Wako Pure Chemical Corporation for testing.

In the experiment, first, a sample (5 μL), buffer (15 μL), DPP-IV (5 μL), and a substrate (25 μL) were added to a 96-well plate and incubated at 37° C. for 30 minutes. Then, the fluorescence intensity was measured by using a fluorometer (Envision 2104 Multilaber Reader, manufactured by Perkin Elmer) (excitation wavelength: 355 nm; fluorescence wavelength: 450 nm).

Next, the fluorescence intensity measured with the addition of ultrapure water (5 μL), buffer (20 μL), and a substrate (25 μL) was subtracted as a background from the fluorescence intensity of each sample. The fluorescence intensity measured with the addition of ultrapure water (5 μL), buffer (15 μL), DPP-IV (5 μL), and a substrate (25 μL) was defined as 100% initial activity.

The inhibition rate was calculated by subtracting the fluorescence intensity of the sample from the fluorescence intensity of 100% initial activity, then dividing the difference by the fluorescence intensity of 100% initial activity, and finally multiplying the quotient by 100. As a positive control, sitagliptin included in the kit was used.

The results are shown in FIG. 1. As shown in FIG. 1, it was found that EGCG and EGCG3"Me have excellent DPP-IV inhibitory activity. In particular, the methylated catechin EGCG3"Me was found to exhibit particularly excellent DPP-IV inhibitory activity.

Subsequently, in this Example, the relationship between the DPP-IV inhibitory activity and the concentration was examined for EGCG3"Me which was found to have extremely excellent DPP-IV inhibitory activity. Specifically, in the experiment described above, the concentration of EGCG3"Me was set to 1 μM, 5 μM, 10 μM, 50 μM, 100 μM or 200 µM, and the DPP-IV inhibitory activity was measured using the DPP (IV) Inhibitor Screening Assay Kit.

The results are shown in FIG. 2. As shown in FIG. 2, it was clarified that the DPP-IV inhibitory activity in EGCG3"Me tends to increase as the concentration increases, and in particular, when it exceeds 50 µM, EGCG3"Me exhibits extremely excellent DPP-IV inhibitory activity.

What is claimed is:

1. A method for inhibiting a dipeptidyl peptidase-IV or an activity of a dipeptidyl peptidase-IV, comprising a step of allowing a subject to intake a dipeptidyl peptidase-IV inhibitor comprising epigallocatechin-3-O-(3-O-methyl)gallate.

2. A method for inhibiting a dipeptidyl peptidase-IV or an activity of a dipeptidyl peptidase-IV, comprising a step of allowing a subject to intake a foodstuff comprising epigallocatechin-3-O-(3-O-methyl)gallate.

* * * * *